(12) United States Patent
Dit Dominique

(10) Patent No.: US 12,415,879 B2
(45) Date of Patent: Sep. 16, 2025

(54) GRAFTED POLYMER CARRYING PENDENT IMIDAZOLE FUNCTIONAL GROUPS

(71) Applicant: COMPAGNIE GENERALE DES ETABLISSEMENTS MICHELIN, Clermont-Ferrand (FR)

(72) Inventor: Francois Jean-Baptiste Dit Dominique, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 877 days.

(21) Appl. No.: 17/618,353

(22) PCT Filed: Jun. 10, 2020

(86) PCT No.: PCT/EP2020/066121
§ 371 (c)(1),
(2) Date: Dec. 10, 2021

(87) PCT Pub. No.: WO2020/249631
PCT Pub. Date: Dec. 17, 2020

(65) Prior Publication Data
US 2022/0235164 A1 Jul. 28, 2022

(30) Foreign Application Priority Data
Jun. 11, 2019 (FR) ..................................... 1906182

(51) Int. Cl.
*C08F 279/04* (2006.01)

(52) U.S. Cl.
CPC .................................. *C08F 279/04* (2013.01)

(58) Field of Classification Search
CPC .... C08F 279/04; C08F 236/10; C08F 279/02; C08F 255/02; C07D 233/60; C07D 233/61; C07D 405/06; C08C 19/22; C08L 51/04; C08L 51/06
See application file for complete search history.

(56) References Cited

U.S. PATENT DOCUMENTS

| | | | |
|---|---|---|---|
| 7,199,175 B2 | 4/2007 | Vasseur |
| 7,900,667 B2 | 3/2011 | Vasseur |
| 9,394,380 B2 | 7/2016 | Araujo Da Silva et al. |
| 10,030,116 B2 | 7/2018 | Salit et al. |
| 10,137,734 B2 | 11/2018 | Gander et al. |
| 10,202,471 B2 | 2/2019 | Ugolnikov et al. |
| 2003/0212185 A1 | 11/2003 | Vasseur |
| 2007/0112120 A1 | 5/2007 | Vasseur |
| 2010/0016349 A1 | 1/2010 | Becker et al. |
| 2013/0131279 A1 | 5/2013 | Araujo Da Silva et al. |
| 2016/0251456 A1 | 9/2016 | Ugolnikov et al. |
| 2016/0264753 A1 | 9/2016 | Salit et al. |
| 2019/0119412 A1 | 4/2019 | Ugolnikov et al. |
| 2022/0098400 A1 | 3/2022 | Jean-Baptiste-Dit-Dominique et al. |
| 2023/0044213 A1 | 2/2023 | Jean-Baptiste-Dit-Dominique et al. |

FOREIGN PATENT DOCUMENTS

| | | | | |
|---|---|---|---|---|
| JP | 2015-44929 A | 3/2015 | | |
| JP | 2016-535744 A | 11/2016 | | |
| JP | 2016-535807 A | 11/2016 | | |
| JP | 2017-501240 A | 1/2017 | | |
| WO | 02/10269 A2 | 2/2002 | | |
| WO | 2012/007441 A1 | 1/2012 | | |
| WO | WO-2015059269 A1 * | 4/2015 | ........... | C07D 233/61 |
| WO | WO-2015059271 A1 * | 4/2015 | ........... | B60C 1/0016 |
| WO | 2020/249623 A1 | 12/2020 | | |

OTHER PUBLICATIONS

International Search Report dated Aug. 26, 2020, in corresponding PCT/EP2020/066121 (4 pages).

* cited by examiner

*Primary Examiner* — Kumar R Bhushan
(74) *Attorney, Agent, or Firm* — VENABLE LLP

(57) ABSTRACT

A modified polymer is obtained by grafting of at least one compound of formula (I) onto at least one unsaturation of the initial polymer chain

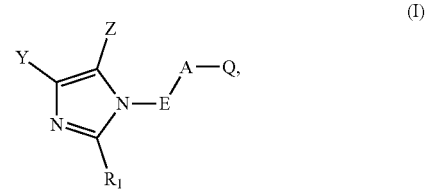

(I)

in which Q represents a dipole comprising at least one nitrogen atom; A represents a divalent heteroaromatic ring optionally substituted with one or more identical or different linear or branched aliphatic hydrocarbon-based chains, optionally substituted or interrupted with one or more heteroatoms; E represents a divalent hydrocarbon-based group which may optionally contain one or more heteroatoms; $R_1$ represents a hydrogen atom or a $C_1$-$C_{20}$ alkyl group; and Y and Z, which may be identical or different, each represent a hydrogen atom or a hydrocarbon-based chain, Y and Z together also possibly forming a ring, notably an aromatic ring, with the carbon atoms of the imidazole ring to which they are attached.

15 Claims, No Drawings

GRAFTED POLYMER CARRYING PENDENT IMIDAZOLE FUNCTIONAL GROUPS

I—FIELD OF THE INVENTION

The present invention relates to novel polymers functionalized by grafting of a 1,3-dipolar compound comprising a heteroaromatic ring and an imidazole function. The invention also relates to a process for obtaining such polymers.

II—TECHNOLOGICAL BACKGROUND

Modifying the structure of a polymer, such as its functionalization by grafting, is particularly sought when it is desired to bring together a polymer and a filler in a composition. This modification may make it possible, for example, to improve the dispersion of the filler in a polymer matrix, thus resulting in a more homogeneous material. The properties of the composition are ultimately improved.

In the case of certain fillers, for instance reinforcing fillers such as carbon black or silica, better dispersion of said filler will generally be reflected by a reduction in the hysteresis of the composition. Such a property is notably sought in rubber compositions intended, for example, for tyre applications. Specifically, reduction of the hysteresis of a rubber composition is favorable towards reducing the rolling resistance of a tyre and thus reducing the fuel consumption of a vehicle driving with such tyres.

It is known that a reduction in hysteresis is often accompanied by a reduction in the stiffness in the cured state of the rubber composition, which may, in certain cases, make the composition unsuitable for the intended use.

It is thus desirable to have available polymers which promote the dispersion of the reinforcing filler without causing an excessive reduction in the stiffness in the cured state of a rubber composition.

Elastomers grafted with a compound of formula Q-A-B in which the group Q comprises a dipole containing at least one nitrogen atom, A is a divalent group which may or may not be aromatic and B is an imidazole function are known from WO 2015/059269 A1. When this grafted elastomer is mixed with reinforcing fillers in a rubber composition, the compromise between stiffness in the cured state and hysteresis of this rubber composition is improved relative to rubber compositions not comprising a grafted elastomer. These grafted elastomers are thus particularly advantageous.

The Applicant continued its research and sought to improve the production of polymers grafted with a compound comprising a dipole containing at least one nitrogen atom and bearing an imidazole function.

After numerous tests, the Applicant has discovered that it can obtain grafted polymers bearing pendent imidazole functional groups with an improved grafting yield relative to the compounds of the prior art and more rapidly by using a family of particular 1,3-dipolar compounds.

III—SUMMARY OF THE INVENTION

One subject of the invention is thus a modified polymer obtained by grafting of at least one compound of formula (I) onto at least one unsaturation of the initial polymer chain

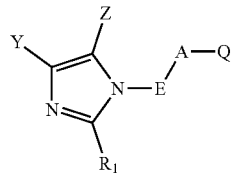

(I)

in which:
Q represents a dipole comprising at least one nitrogen atom;
A represents a divalent heteroaromatic ring optionally substituted with one or more identical or different aliphatic hydrocarbon-based chains, which are preferably saturated, linear or branched, optionally substituted or interrupted with one or more heteroatoms;
E represents a divalent hydrocarbon-based group which may optionally contain one or more heteroatoms;
$R_1$ represents a hydrogen atom or a $C_1$-$C_{20}$ alkyl group; and
Y and Z, which may be identical or different, each represent a hydrogen atom or a hydrocarbon-based chain, Y and Z together also possibly forming a ring, notably an aromatic ring, with the carbon atoms of the imidazole ring to which they are attached.

Advantageously, the compound of formula (I) makes it possible to obtain modified polymers by grafting and bearing pendent imidazole functional groups more rapidly and with a better yield than the compounds of the prior art.

In the present document, unless expressly indicated otherwise, all the percentages (%) indicated are percentages (%) by mass.

Moreover, any interval of values denoted by the expression "between a and b" represents the range of values extending from more than a to less than b (that is to say, limits a and b excluded), whereas any interval of values denoted by the expression "from a to b" means the range of values extending from a up to b (that is to say, including the strict limits a and b). In the present document, when an interval of values is denoted by the expression "from a to b", the interval represented by the expression "between a and b" is also and preferentially denoted.

Unless otherwise mentioned, the term "heteroatom" means an atom chosen from the group consisting of a sulfur atom, an oxygen atom and a nitrogen atom.

The compounds comprising carbon mentioned in the description may be of fossil origin or biosourced. In the latter case, they may be partially or completely derived from biomass or may be obtained from renewable starting materials derived from biomass. Polymers, plasticizers, fillers, etc. are notably concerned.

The invention and the advantages thereof will be readily understood in the light of the description and the implementation examples that follow.

IV—DETAILED DESCRIPTION OF THE INVENTION

As explained previously, one subject of the invention is thus a modified polymer obtained by grafting of at least one compound of formula (I) onto at least one unsaturation of the initial polymer chain

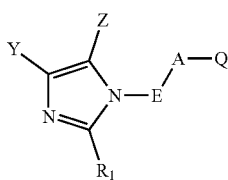

(I)

in which:
- Q represents a dipole comprising at least one nitrogen atom;
- A represents a divalent heteroaromatic ring optionally substituted with one or more identical or different linear or branched aliphatic hydrocarbon-based chains, optionally substituted or interrupted with one or more heteroatoms;
- E represents a divalent hydrocarbon-based group which may optionally contain one or more heteroatoms;
- $R_1$ represents a hydrogen atom or a $C_1$-$C_{20}$ alkyl group; and
- Y and Z, which may be identical or different, each represent a hydrogen atom or a hydrocarbon-based chain, Y and Z together also possibly forming a ring, notably an aromatic ring, with the carbon atoms of the imidazole ring to which they are attached.

The term "modified polymer obtained by grafting" or "polymer modified by grafting" refers to a polymer including functions, notably imidazole functions, which have been introduced into the polymer chain. In practice, the modified polymer is obtained by grafting reaction of a compound bearing imidazole functions and bearing a function that is capable of forming a covalent bond with an unsaturation of the polymer chain, this function being a dipole comprising at least one nitrogen atom, preferably a nitrone. During the grafting reaction, the dipole comprising at least one nitrogen atom of the compound to be grafted forms covalent bonds with an unsaturation of the polymer chain.

As is known, a polymer generally comprises at least one main polymer chain. This polymer chain may be termed the main chain as long as all the other chains of the polymer are considered to be pendent chains, as mentioned in the document "Glossary of basic terms in polymer science" (IUPAC recommendations 1996), PAC, 1996, 68, 2287, page 2294.

The term "unsaturation" means a multiple covalent bond between two carbon atoms: this multiple covalent bond may be a carbon-carbon double bond or a carbon-carbon triple bond, preferably a carbon-carbon double bond.

For the purposes of the present invention, the term "initial polymer chain" means the polymer chain before the grafting reaction; this chain comprises at least one unsaturation that is capable of reacting with the compound of formula (I) described above. The initial polymer is thus the polymer serving as the starting reagent during the grafting reaction. The grafting reaction makes it possible, starting with an initial polymer, to obtain a modified polymer.

Preferably, this initial polymer is an elastomer, even more preferentially a diene elastomer.

The term "diene elastomer" (or, without distinction, rubber), whether natural or synthetic, should be understood, in a known manner, as meaning an elastomer consisting, at least partly (i.e., a homopolymer or a copolymer) of diene monomer units (monomers bearing two conjugated or non-conjugated carbon-carbon double bonds).

These diene elastomers may be classified into two categories: "essentially unsaturated" or "essentially saturated".

The term "essentially unsaturated" generally refers to a diene elastomer at least partly derived from conjugated diene monomers having a content of units of diene origin (conjugated dienes) which is greater than 15% (mol %); thus it is that diene elastomers such as butyl rubbers or copolymers of dienes and of α-olefins of EPDM type do not come within the preceding definition and may notably be described as "essentially saturated" diene elastomers (low or very low content, always less than 15%, of units of diene origin).

The term "diene elastomer that may be used in the context of the present invention" particularly means:
- any homopolymer of a conjugated or non-conjugated diene monomer containing from 4 to 18 carbon atoms;
- any copolymer of a conjugated or non-conjugated diene containing from 4 to 18 carbon atoms and of at least one other monomer.

The other monomer may be ethylene, an olefin or a conjugated or non-conjugated diene.

Conjugated dienes that are suitable include conjugated dienes containing from 4 to 12 carbon atoms, in particular 1,3-dienes, notably such as 1,3-butadiene and isoprene.

Non-conjugated dienes that are suitable include non-conjugated dienes containing from 6 to 12 carbon atoms, such as 1,4-hexadiene, ethylidenenorbornene or dicyclopentadiene.

Olefins that are suitable include vinylaromatic compounds containing from 8 to 20 carbon atoms and aliphatic α-monoolefins containing from 3 to 12 carbon atoms.

Vinylaromatic compounds that are suitable include, for example, styrene, ortho-, meta- or para-methylstyrene, the "vinyltoluene" commercial mixture or para-(tert-butyl)styrene.

Aliphatic α-monoolefins that are suitable notably include acyclic aliphatic α-monoolefins containing from 3 to 18 carbon atoms.

More particularly, the diene elastomer may be:
- any homopolymer of a conjugated diene monomer, notably any homopolymer obtained by polymerization of a conjugated diene monomer containing from 4 to 12 carbon atoms;
- any copolymer obtained by copolymerization of one or more conjugated dienes with each other or with one or more vinylaromatic compounds containing from 8 to 20 carbon atoms;
- a copolymer of isobutene and of isoprene (butyl rubber) and also the halogenated versions, in particular chlorinated or brominated versions, of this type of copolymer;
- any copolymer obtained by copolymerization of one or more conjugated or non-conjugated dienes with ethylene, an α-monoolefin or a mixture thereof, for instance the elastomers obtained from ethylene, from propylene with a non-conjugated diene monomer of the above-mentioned type.

Preferentially, the initial polymer is preferably a diene elastomer chosen from the group consisting of ethylene/propylene/diene monomer (EPDM) copolymers, butyl rubber (IRR), natural rubber (NR), synthetic polyisoprenes (IRs), polybutadienes (BRs), butadiene copolymers, isoprene copolymers and mixtures of these elastomers.

Preferentially, the initial polymer is preferably a diene elastomer chosen from the group consisting of ethylene/propylene/diene monomer (EPDM) copolymers, butyl rubber (IRR), natural rubber (NR), synthetic polyisoprenes (IRs), polybutadienes (BRs), butadiene/styrene copolymers (SBRs), ethylene/butadiene copolymers (EBRs), isoprene/ butadiene copolymers (BIRs) or isoprene/butadiene/styrene copolymers (SBIRs), isobutene/isoprene copolymers (butyl rubber-IIR), isoprene/styrene copolymers (SIRs), and mixtures of these elastomers.

Preferentially, the initial polymer is preferably a diene elastomer chosen from the group consisting of ethylene/propylene/diene monomer copolymers, butyl rubber, and a mixture of these rubbers.

Preferentially, the initial polymer is preferably a diene elastomer chosen from the group consisting of natural rubber, synthetic polyisoprenes, polybutadienes, butadiene copolymers, isoprene copolymers and mixtures of these elastomers.

More preferentially, the initial polymer is preferably a diene elastomer chosen from the group consisting of natural rubber, synthetic polyisoprenes, polybutadienes, butadiene/styrene copolymers, ethylene/butadiene copolymers, isoprene/butadiene copolymers, isoprene/butadiene/styrene copolymers, isobutene/isoprene copolymers, isoprene/styrene copolymers, and mixtures of these elastomers.

Preferentially, the initial polymer is preferably a diene elastomer chosen from the group consisting of polybutadienes, butadiene copolymers, isoprene copolymers and mixtures of these elastomers.

More preferentially, the initial polymer is a diene elastomer chosen from the group consisting of polybutadienes, butadiene/styrene copolymers, ethylene/butadiene copolymers, isoprene/butadiene copolymers, isoprene/butadiene/styrene copolymers, isobutene/isoprene copolymers, isoprene/styrene copolymers, and mixtures of these elastomers.

The following are suitable: polybutadienes and in particular those with a content (mol %) of 1,2-units of between 4% and 80% or those with a content (mol %) of cis-1,4-units of greater than 80%, polyisoprenes, butadiene/styrene copolymers and in particular those with a Tg (glass transition temperature (Tg, measured according to ASTM D3418 (2014)) of between 0° C. and −90° C. and more particularly between −10° C. and −70° C., a styrene content of between 1% and 60% by weight and more particularly between 20% and 50%, a content (mol %) of 1,2-bonds of the butadiene part of between 4% and 75% and a content (mol %) of trans-1,4-bonds of between 10% and 80%, butadiene/isoprene copolymers and notably those with an isoprene content of between 5% and 90% by weight and a Tg of from −40° C. to −80° C., or isoprene/styrene copolymers and notably those with a styrene content of between 5% and 50% by weight and a Tg of between −5° C. and −50° C. In the case of the butadiene/styrene/isoprene copolymers, those with a styrene content of between 5% and 50% by weight and more particularly of between 10% and 40%, an isoprene content of between 15% and 60% by weight and more particularly of between 20% and 50%, a butadiene content of between 5% and 50% by weight and more particularly of between 20% and 40%, a content (mol %) of 1,2-units of the butadiene part of between 4% and 85%, a content (mol %) of trans-1,4-units of the butadiene part of between 6% and 80%, a content (mol %) of 1,2-plus 3,4-units of the isoprene part of between 5% and 70% and a content (mol %) of trans-1,4-units of the isoprene part of between 10% and 50%, and more generally any butadiene/styrene/isoprene copolymer with a Tg of between −5° C. and −70° C., are notably suitable.

The initial polymers that may be used in the context of the invention, preferably the elastomers, more preferentially the diene elastomers, may have any microstructure which is a function of the polymerization conditions used. The polymers may be, for example, block, random, sequential or microsequential polymers and may be prepared in dispersion, in emulsion or in solution. They may be coupled and/or star-branched, for example by means of a silicon or tin atom which connects the polymer chains together.

According to the invention, the initial polymer, preferably the elastomer, even more preferentially the diene elastomer, is modified by grafting of a compound of formula (I) as defined above, also known as a modifying agent.

In accordance with formula (I), this modifying agent contains a group Q denoting a dipole comprising at least one nitrogen atom.

For the purposes of the present invention, the term "dipole" means a function that is capable of forming a 1,3-dipolar addition on an unsaturated carbon-carbon bond.

Preferably, the dipole comprising at least one nitrogen atom is chosen from the group consisting of nitrile oxide, nitrone and nitrile imine.

For the purposes of the present invention, the term "nitrile oxide" means a dipole corresponding to the formula C≡N→O, including the mesomeric forms thereof.

For the purposes of the present invention, the term "nitrile imine" means a dipole corresponding to the formula C≡N→N, including the mesomeric forms thereof.

For the purposes of the present invention, the term "nitrone" means a dipole corresponding to the formula —C=N(→O)—, including the mesomeric forms thereof.

More preferentially, Q is a group of formula (II), (III) or (IV)

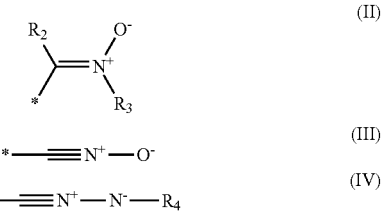

in which:
the symbol * represents the attachment of Q to A; and
$R_2$ and $R_4$ are chosen, independently of each other, from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched;
$R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

Preferably, $R_2$ and $R_4$ are chosen, independently of each other, from a hydrogen atom, a linear or branched $C_1$-$C_{20}$ alkyl, a $C_3$-$C_{30}$ cycloalkyl optionally with one or more linear or branched $C_1$-$C_6$ alkyls, a $C_6$-$C_{20}$ aryl optionally substituted with one or more linear or branched $C_1$-$C_6$ alkyls and $R_3$ is chosen from the group consisting of linear or branched $C_1$-$C_{20}$ alkyls, $C_3$-$C_{20}$ cycloalkyls optionally substituted with one or more linear or branched $C_1$-$C_6$ alkyls, and $C_6$-$C_{20}$ aryls optionally substituted with one or more linear or branched $C_1$-$C_6$ alkyls.

Preferentially, the compound of formula (I) is chosen from the compounds of formula (IIa)

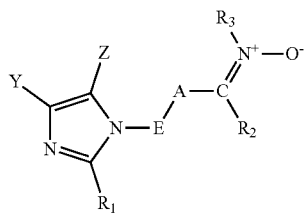

(IIa)

in which:
- A represents a divalent heteroaromatic ring optionally substituted with one or more identical or different aliphatic hydrocarbon-based chains, which are preferably saturated, linear or branched, optionally substituted or interrupted with one or more heteroatoms;
- E represents a divalent hydrocarbon-based group which may optionally contain one or more heteroatoms;
- $R_1$ represents a hydrogen atom or a $C_1$-$C_{20}$ alkyl group;
- Y and Z, which may be identical or different, each represent a hydrogen atom or a hydrocarbon-based chain, Y and Z together also possibly forming a ring, notably an aromatic ring, with the carbon atoms of the imidazole ring to which they are attached;
- $R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and
- $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

The compounds of the invention of formulae (I) and (IIa) contain a group A which represents a divalent heteroaromatic ring optionally substituted with one or more identical or different hydrocarbon-based chains, optionally substituted or interrupted, independently of each other, with one or more heteroatoms.

The term "divalent heteroaromatic ring" means an aromatic ring system comprising one or more heteroatoms chosen from the group consisting of nitrogen, sulfur and oxygen. This system may be monocyclic or bicyclic and may be formed from 5 to 10 atoms. Preferably, this system is monocyclic and is formed from 5 to 6 atoms. This system may optionally be substituted with one or more identical or different aliphatic hydrocarbon-based chains, which are preferably saturated, linear or branched, optionally substituted or interrupted with one or more heteroatoms, for instance O, N and S.

Preferably, when the divalent heteroaromatic ring is substituted with one or more identical or different linear or branched aliphatic hydrocarbon-based chains, optionally substituted or interrupted with one or more heteroatoms, this or these chains are preferably inert with respect to the imidazole ring bearing the substituents $R_1$, X and Y and with respect to the group Q.

For the purposes of the present invention, the term "hydrocarbon-based chain(s) which is (are) inert with respect to the imidazole ring bearing the substituents $R_1$, X and Y and with respect to the group Q" means a hydrocarbon-based chain which does not react either with said imidazole heterocycle or with said group Q. Thus, said hydrocarbon-based chain which is inert with respect to said heterocycle and with respect to said group is, for example, a hydrocarbon-based chain which does not bear any alkenyl or alkynyl functions which are capable of reacting with said ring or with said group. Preferably, these hydrocarbon-based chains include from 1 to 24 carbon atoms and are saturated.

Preferably, A is a divalent heteroaromatic ring formed from 5 to 10 atoms, preferably from 5 to 6 atoms, optionally substituted with one or more identical or different $C_1$-$C_{24}$ aliphatic hydrocarbon-based chains, which are preferably saturated, linear or branched, optionally substituted or interrupted with one or more heteroatoms.

Even more preferentially, in the compounds of formulae (I) and (IIa), A is a divalent heteroaromatic ring formed from 5 to 10 atoms, preferably from 5 to 6 atoms, optionally substituted with one or more substituents chosen from the group consisting of linear or branched $C_1$-$C_{12}$ (more preferentially $C_1$-$C_6$ and even more preferentially $C_1$-$C_4$) alkyls, groups —OR', groups —NHR', groups —SR' in which R' is a $C_1$-$C_{12}$, preferably $C_1$-$C_6$ and even more preferentially $C_1$-$C_4$ alkyl group.

More preferentially, in the compounds of formulae (I) and (IIa), A is chosen from furan-diyl, thiophene-diyl, pyrrole-diyl, thiazole-diyl, imidazole-diyl, pyridine-diyl, pyrazine-diyl, pyrimidine-diyl, indole-diyl, benzofuran-diyl, isoindole-diyl, isobenzofuran-diyl and benzothiophene-diyl; these rings are optionally substituted with one or more identical or different aliphatic hydrocarbon-based chains, which are preferably saturated, optionally substituted or interrupted with one or more heteroatoms, for instance O, N and S; more preferentially, these rings may be substituted with one or more $C_1$-$C_6$ alkyls. Even more preferentially, these rings are unsubstituted.

More preferentially, in the compounds of formulae (I) and (IIa), A is chosen from furan-diyl, thiophene-diyl and pyrrole-diyl, and even more preferentially is furan-diyl.

Among the compounds of formula (IIa), particular preference is given to those of formula (IIb)

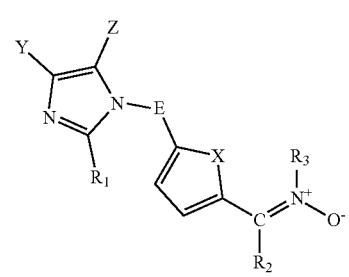

(IIb)

in which:
- X represents a heteroatom chosen from a sulfur atom, an oxygen atom and a nitrogen atom; preferably, X is an oxygen atom;
- E represents a divalent hydrocarbon-based group which may optionally contain one or more heteroatoms;
- $R_1$ represents a hydrogen atom or a $C_1$-$C_{20}$ alkyl group;
- Y and Z, which may be identical or different, each represent a hydrogen atom or a hydrocarbon-based group, Y and Z together also possibly forming a ring, notably an aromatic ring, with the carbon atoms of the imidazole ring to which they are attached;

$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

The compounds of the invention of formulae (I), (IIa) and (IIb) contain a group E which represents a divalent hydrocarbon-based bonding group which may optionally contain one or more heteroatoms. For the purposes of the present invention, the term "divalent hydrocarbon-based bonding group" means a spacer group forming a bridge between the group A and the imidazole ring bearing the substituents $R_1$, X and Y, this spacer group being a linear or branched, preferably saturated, preferably $C_1$-$C_{24}$ aliphatic hydrocarbon-based chain which may optionally contain one or more heteroatoms, for instance N, O and S. Said hydrocarbon-based chain may optionally be substituted, provided that the substituents do not react with the group Q and the imidazole ring bearing the substituents $R_1$, X and Y.

Preferentially, in the compounds of the invention of formulae (I), (IIa) and (IIb), E is chosen from linear or branched, saturated, $C_1$-$C_{24}$, more preferentially $C_1$-$C_{10}$ and even more preferentially $C_1$-$C_6$ aliphatic hydrocarbon-based chains optionally interrupted with one or more heteroatoms such as N, S and O.

Preferably, in the compounds of the invention of formulae (I), (IIa) and (IIb), E is chosen from the group consisting of —R—, —NH—R—, —O—R— and —S—R—, R being a linear or branched $C_1$-$C_{24}$, preferably $C_1$-$C_{10}$ and more preferentially $C_1$-$C_6$, alkylene.

Even more preferentially, in the compounds of the invention of formulae (I), (IIa) and (IIb), E is chosen from the group consisting of —R— and —O—R—, R being a linear or branched $C_1$-$C_{24}$, preferably $C_1$-$C_{10}$ and more preferentially $C_1$-$C_6$, alkylene.

Even more preferentially, in the compounds of the invention of formulae (I), (IIa) and (IIb), E is chosen from —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —O—CH$_2$—CH$_2$—, —O—CH$_2$—CH$_2$—CH$_2$— and —O—CH$_2$—CH$_2$—CH$_2$—CH$_2$—.

Even more preferentially, in the compounds of the invention of formulae (I), (IIa) and (IIb), E is chosen from a linear or branched $C_1$-$C_{24}$, preferably $C_1$-$C_{10}$ and more preferentially $C_1$-$C_6$ alkylene, and even more preferentially is chosen from —CH$_2$—, —CH$_2$—CH$_2$—, —CH$_2$—CH$_2$—CH$_2$— and —CH$_2$—CH$_2$—CH$_2$—CH$_2$—.

Even more preferentially, in the compounds of the invention of formulae (I) and (IIa), E is chosen from —CH$_2$—, —CH$_2$—CH$_2$—, —CH$_2$—CH$_2$—CH$_2$— and —CH$_2$—CH$_2$—CH$_2$—CH$_2$—.

The compounds of the invention of formulae (I), (IIa) and (IIb) contain a group $R_1$ which represents a hydrogen atom or a $C_1$-$C_{20}$ alkyl group. Preferentially, in the compounds of the invention of formulae (I), (IIa) and (IIb), $R_1$ represents a hydrogen atom or a $C_1$-$C_6$ alkyl group, preferably methyl. These alkyl groups may be linear or branched.

The compounds of the invention of formulae (I), (IIa) and (IIb) contain groups Y and Z, which may be identical or different, which each represent a hydrogen atom or a hydrocarbon-based chain, Y and Z together also possibly forming a ring, notably an aromatic ring, with the carbon atoms of the imidazole ring to which they are attached.

Preferentially, in the compounds of the invention of formulae (I), (IIa) and (IIb), Y and Z, which may be identical or different, each represent a hydrogen atom or a linear or branched $C_1$-$C_{24}$, preferably $C_1$-$C_{10}$ and more preferentially $C_1$-$C_6$ alkyl, Y and Z together also possibly forming a ring, notably an aromatic ring, with the carbon atoms of the imidazole ring to which they are attached.

According to a preferred embodiment, in the compounds of the invention of formulae (I), (IIa) and (IIb), Y and Z are a hydrogen atom.

According to another preferred embodiment, in the compounds of the invention of formulae (I), (IIa) and (IIb), Y and Z together form an aromatic ring with the carbon atoms of the imidazole ring to which they are attached; preferably, Y and Z form a benzene ring with the carbon atoms of the imidazole ring to which they are attached.

Preferentially, in the compounds of formulae (IIa) and (IIb), $R_2$ represents a hydrogen atom or a group chosen from linear or branched $C_1$-$C_{20}$ alkyls, $C_3$-$C_{20}$ cycloalkyls optionally substituted with a $C_1$-$C_6$ alkyl, or $C_6$-$C_{20}$ aryls optionally substituted with a $C_1$-$C_6$ alkyl.

Preferentially, in the compounds of formulae (IIa) and (IIb), $R_3$ is chosen from linear or branched $C_1$-$C_{20}$ alkyls, $C_3$-$C_{20}$ cycloalkyls optionally substituted with a $C_1$-$C_6$ alkyl, or $C_6$-$C_{20}$ aryls optionally substituted with a $C_1$-$C_6$ alkyl.

Even more preferentially, in the compounds of formulae (IIa) and (IIb), $R_2$ is a hydrogen atom and $R_3$ is chosen from $C_1$-$C_{20}$ alkyls and $C_6$-$C_{20}$ aryls.

Even more preferentially, in the compounds of formulae (IIa) and (IIb), $R_2$ is a hydrogen atom and $R_3$ is phenyl.

Among the compounds of formulae (I), (IIa) and (IIb), particular preference is given to the compound of formula (VIII)

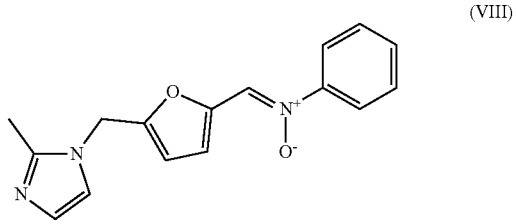 [SMILES: Cc1nccn1Cc1ccc(/C=[N+](\[O-])c2ccccc2)o1]

(VIII)

Surprisingly, the compound of formula (I), preferably the compound of formula (IIa) or (IIb), even more preferentially the compound of formula (VII), makes it possible to obtain polymers modified by grafting and bearing pendent imidazole functional groups more rapidly and in a better yield than the compounds of the prior art.

The modifying agents of formula (IIa) and the preferred embodiments thereof may be obtained, for example, by means of a process for preparing a compound (IIa) as defined above, said process comprising at least one reaction (c) of a compound of formula (III) with a compound of formula (IV) according to the following reaction scheme

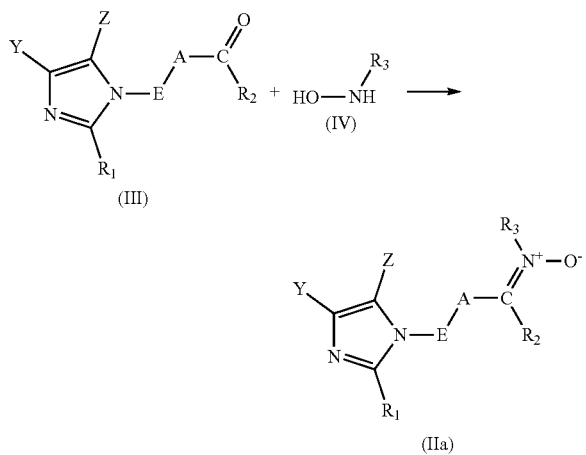

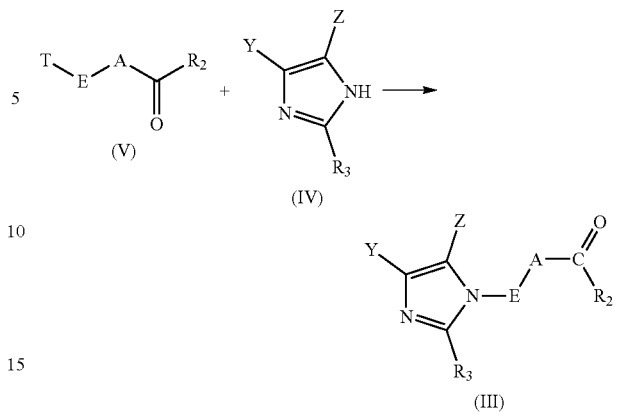

with, in formulae (IIa), (III) and (IV):

A represents a divalent heteroaromatic ring optionally substituted with one or more identical or different aliphatic hydrocarbon-based chains, which are preferably saturated, linear or branched, optionally substituted or interrupted with one or more heteroatoms;

E represents a divalent hydrocarbon-based group which may optionally contain one or more heteroatoms;

$R_1$ represents a hydrogen atom or a $C_1$-$C_{20}$ alkyl group;

Y and Z, which may be identical or different, each represent a hydrogen atom or a hydrocarbon-based group, Y and Z together also possibly forming a ring, notably an aromatic ring, with the carbon atoms of the imidazole ring to which they are attached;

$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

Preferred forms of A, E, $R_1$, $R_2$, $R_3$, Y and Z also apply to the process for preparing a compound of formula (IIa) from a compound of formula (III) and of formula (IV).

A person skilled in the art knows how to adapt the reaction described above to obtain the compounds of formula (I) according to the invention from the compound of formula (III).

The compound of formula (IV) is commercially available from suppliers such as Sigma-Aldrich, Fischer, etc.

The process for preparing the compound for preparing a compound (IIa) as defined above also comprises at least one reaction (b) of a compound of formula (V) with at least one compound of formula (IV) to form the compound of formula (III)

with:

the groups E, A, $R_1$, $R_2$, $R_3$, Y and Z being as defined previously, including the preferred forms thereof, and the group T is chosen from chlorine, bromine, iodine, fluorine, the mesylate group, the tosylate group, the acetate group and the trifluoromethylsulfonate group.

The compound of formula (IV) is commercially available from chemical product suppliers such as Aldrich, ABCR, etc.

The process for preparing the compound for preparing a compound (IIa) as defined above also comprises at least one reaction (a) of electrophilic activation of the compound of formula (VII) to form the compound of formula (V) in the presence of an electrophilic activating agent according to the following reaction scheme:

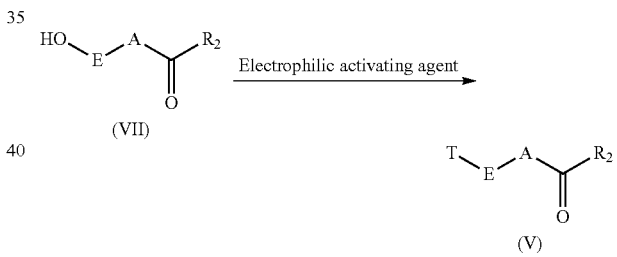

with
the groups E, A and $R_2$ as defined above, including the preferred forms thereof, T being a leaving group provided by the electrophilic activating agent.

the group T is chosen from chlorine, bromine, iodine, fluorine, the mesylate group, the tosylate group, the acetate group and the trifluoromethylsulfonate group.

The term "hydrophilic activating agent" means an agent which reacts with a hydroxyl group —OH, giving it an electrophilic nature. These electrophilic activating agents and this electrophilic activation reaction on a hydroxyl group are well known to those skilled in the art. Examples of electrophilic activating agents that may be mentioned include thionyl chloride, mesyl chloride, 4-toluenesulfonyl chloride, para-toluenesulfonyl chloride, etc.

Preferentially, the leaving group T provided by the electrophilic agent is chosen from the group consisting of chlorine, bromine, iodine, the mesylate group and the tosylate group.

The compounds of formulae (VII) and (VI) are commercially available from chemical product suppliers such as Aldrich, ABCR, etc.

According to a preferential embodiment, the process for preparing a compound of formula (IIa) comprises at least the following successive reactions: reaction (b) followed by reaction (c) as defined previously.

According to another preferential embodiment, the process for preparing a compound of formula (IIa) comprises at least the following successive reactions: reaction (a) followed by reaction (b) followed by reaction (c) as defined previously.

According to another preferential embodiment, the process for preparing a compound of formula (IIa) comprises at least the following successive reactions: reaction (a) followed by reaction (b) followed by reaction (c) as defined previously. Preferentially, in this embodiment, the compound of formula (VII) is obtained by dehydration of fructose or glucose; even more preferentially, the compound of formula (VII) is obtained by dehydration of biosourced fructose or of biosourced glucose. For the purposes of the present invention, the terms "biosourced fructose" and "biosourced glucose" mean fructose and glucose obtained from biomass which may be differentiated, respectively, from fructose and glucose synthesized from fossil starting materials by the methods described in the standard ASTM D6866-12.

As explained previously, the compounds of formula (I), in particular those of formula (IIa), more particularly those of formula (IIb) and even more particularly the compound of formula (VII), are used as polymer-modifying agents. They may be grafted onto one or more polymers comprising at least one unsaturated carbon-carbon bond; in particular, this polymer may be an elastomer and more particularly a diene elastomer as defined previously. The compounds of formula (I), in particular those of formula (IIa) or (IIb), in particular those of formula (VII), advantageously have improved kinetics of grafting onto polymers relative to the compounds of the prior art.

A subject of the invention is also a process for preparing a modified polymer, said process comprising a step of grafting, onto an initial polymer comprising at least one unsaturation, of a compound of formula (I), in particular the compound of formula (IIa), more particularly the compound of formula (IIb), even more particularly the compound of formula (VII), as defined above, including the preferred embodiments thereof, by [3+2] cycloaddition of the group Q of the compound of formula (I), or, respectively, of the nitrone of the compound of formula (IIa) or of the compound of formula (IIb), even more particularly the compound of formula (VII) on said unsaturation.

The grafting of these compounds is performed by [3+2] cycloaddition of the group Q (or, respectively, of the nitrone) of said compounds onto an unsaturated carbon-carbon bond of the polymer chain. The mechanism of this cycloaddition is notably illustrated in WO 2012/007441. During this reaction, said compound of formula (I), in particular the compound of formula (IIa) or the compound of formula (IIb), even more particularly the compound of formula (VII), forms covalent bonds with the polymer chain.

According to the invention, the polymer bears, along the main polymer chain, one or more pendent groups derived from the grafting reaction of the compounds of formula (I), in particular of the compound of formula (IIa), more particularly the compound of formula (IIb), even more particularly the compound of formula (VII), as defined above.

Advantageously, these pendent groups are distributed randomly along the main polymer chain.

According to a preferred embodiment, the molar degree of grafting of the compound of formula (I), in particular the compound of formula (IIa), more particularly the compound of formula (IIb), even more particularly the compound of formula (VII), is in a range extending from 0.01% to 15%, preferably from 0.05% to 10%, more preferentially from 0.07% to 5%.

The term "molar degree of grafting" means the number of moles of compound of formula (I), in particular the compound of formula (IIa), more particularly the compound of formula (IIb), even more particularly the compound of formula (VII), grafted onto the polymer per 100 mol of monomer units constituting the initial polymer. The molar degree of grafting can be determined by conventional polymer analysis methods, for instance $^1$H NMR analysis.

According to one embodiment of the process for preparing a modified polymer, the grafting of the compound of formula (I), in particular of the compound of formula (IIa), more particularly the compound of formula (IIb), even more particularly the compound of formula (VII), may be performed in bulk, for example in an extruder, an internal mixer or in an external mixer such as a roll mill, or in solution.

According to another embodiment, the process for preparing a modified polymer may be performed in solution continuously or batchwise. The polymer thus obtained by grafting may be separated from its solution by any type of means known to those skilled in the art and in particular by a steam stripping operation.

Preferably, in the process of the invention, the initial polymer is an elastomer, even more preferentially a diene elastomer.

A subject of the invention is also a composition comprising at least one modified polymer obtained by grafting of the compound of formula (I), preferably of formula (Ia) or (Ib), even more preferentially of formula (VIII) as described above and at least one additive.

The additives that may be used in the composition according to the invention may be plasticizers (such as plasticizing oils and/or plasticising resins), fillers (reinforcing or non-reinforcing fillers), pigments, protective agents such as antiozone waxes, chemical antiozonants, antioxidants, antifatigue agents, reinforcing resins (as described, for example, in patent application WO 02/10269), a crosslinking system, for example based on sulfur and other vulcanizing agents, and/or peroxide and/or bismaleimide. Preferably, this additive is a reinforcing filler, more preferentially this additive is an inorganic reinforcing filler, and even more preferentially this additive is a silica.

In addition to the subjects described previously, the invention relates to at least one of the subjects described in the following embodiments:

1. Modified polymer obtained by grafting of at least one compound of formula (I) onto at least one unsaturation of the initial polymer chain

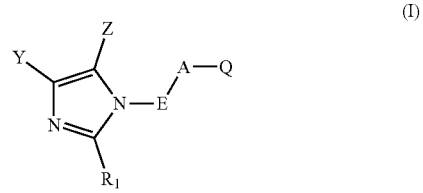

(I)

in which:

Q represents a dipole comprising at least one nitrogen atom;

A represents a divalent heteroaromatic ring optionally substituted with one or more identical or different linear or branched aliphatic hydrocarbon-based chains, optionally substituted or interrupted with one or more heteroatoms;

E represents a divalent hydrocarbon-based group which may optionally contain one or more heteroatoms;

$R_1$ represents a hydrogen atom or a $C_1$-$C_{20}$ alkyl group; and

Y and Z, which may be identical or different, each represent a hydrogen atom or a hydrocarbon-based chain, Y and Z together also possibly forming a ring, notably an aromatic ring, with the carbon atoms of the imidazole ring to which they are attached.

2. Modified polymer according to embodiment 2, in which the molar degree of grafting of the compound of formula (I) is in a range extending from 0.01% to 15%, preferably from 0.05% to 10%, more preferentially from 0.07% to 5%.

3. Modified polymer according to either of embodiments 1 and 2, in which the group Q is a group of formula (II), (III) or (IV)

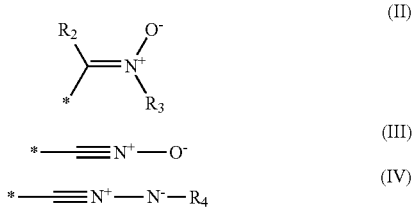

in which:
the symbol * represents the attachment of Q to A;

$R_2$ and $R_4$ are chosen, independently of each other, from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

4. Modified polymer according to embodiment 3, in which the compound of formula (I) is chosen from the compounds of formula (IIa)

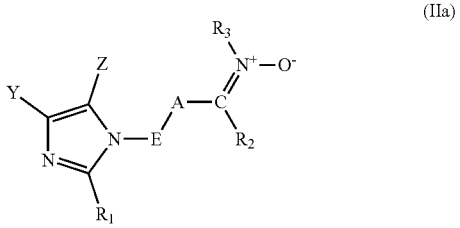

in which:
A represents a divalent heteroaromatic ring optionally substituted with one or more identical or different linear or branched aliphatic hydrocarbon-based chains, optionally substituted or interrupted with one or more heteroatoms;

E represents a divalent hydrocarbon-based group which may optionally contain one or more heteroatoms;

$R_1$ represents a hydrogen atom or a $C_1$-$C_{20}$ alkyl group;

Y and Z, which may be identical or different, each represent a hydrogen atom or a hydrocarbon-based chain, Y and Z together also possibly forming a ring, notably an aromatic ring, with the carbon atoms of the imidazole ring to which they are attached;

$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

5. Modified polymer according to any one of embodiments 1 to 4, in which the group A is a divalent heteroaromatic ring formed from 5 to 10 atoms, preferably from 5 to 6 atoms, optionally substituted with one or more identical or different linear or branched, aliphatic $C_1$-$C_{24}$ hydrocarbon-based chains, optionally substituted or interrupted with one or more heteroatoms.

6. Modified polymer according to any one of embodiments 1 to 5, in which the group A is chosen from furan-diyl, thiophene-diyl, pyrrole-diyl, thiazole-diyl, imidazole-diyl, pyridine-diyl, pyrazine-diyl, pyrimidine-diyl, indole-diyl, benzofuran-diyl, isoindole-diyl, isobenzofuran-diyl and benzothiophene-diyl.

7. Modified polymer according to embodiment 4, in which the compound of formula (IIa) is chosen from those of formula (IIb)

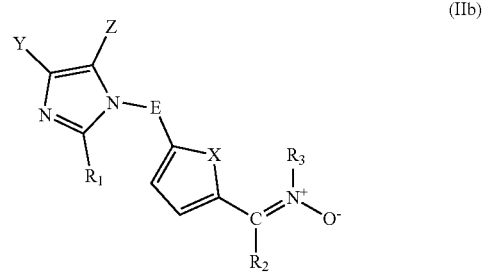

in which:
X represents a heteroatom group chosen from a sulfur atom, an oxygen atom and a nitrogen atom; preferably, X is an oxygen atom;

E represents a divalent hydrocarbon-based group which may optionally contain one or more heteroatoms;

$R_1$ represents a hydrogen atom or a $C_1$-$C_{20}$ alkyl group;

Y and Z, which may be identical or different, each represent a hydrogen atom or a hydrocarbon-based chain, Y and Z together also possibly forming a ring, notably an aromatic ring, with the carbon atoms of the imidazole ring to which they are attached;

$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and $R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

8. Modified polymer according to any one of embodiments 3 to 7, in which $R_2$ is a hydrogen atom and $R_3$ is chosen from $C_1$-$C_{20}$ alkyls and $C_6$-$C_{20}$ aryls.

9. Modified polymer according to any one of the preceding embodiments, in which the group E is chosen from linear or branched, saturated aliphatic $C_1$-$C_{24}$, preferentially $C_1$-$C_{10}$, more preferentially $C_1$-$C_6$, hydrocarbon-based chains optionally interrupted with one or more nitrogen, sulfur or oxygen atoms.

10. Modified polymer according to any one of the preceding embodiments, in which the group E is chosen from the groups —R—, —NHR—, —OR— and —SR—, where R is a linear or branched $C_1$-$C_{24}$, preferably $C_1$-$C_{10}$ and more preferentially $C_1$-$C_6$ alkylene.

11. Modified polymer according to any one of the preceding embodiments, in which the group E is chosen from the groups —R— and —OR—, where R is a linear or branched $C_1$-$C_{24}$, preferably $C_1$-$C_{10}$ and more preferentially $C_1$-$C_6$ alkylene.

12. Modified polymer according to any one of the preceding embodiments, in which the group E is a linear or branched $C_1$-$C_{24}$, preferably $C_1$-$C_{10}$ and more preferentially $C_1$-$C_6$ alkylene, even more preferentially chosen from —$CH_2$—, —$CH_2$—$CH_2$—, —$CH_2$—$CH_2$—$CH_2$— and —$CH_2$—$CH_2$—$CH_2$—$CH_2$—.

13. Modified polymer according to any one of the preceding embodiments, in which the groups Y and Z, which may be identical or different, each represent a hydrogen atom or a $C_1$-$C_{24}$, preferably $C_1$-$C_{10}$ and more preferentially $C_1$-$C_6$ alkyl, Y and Z together also possibly forming a ring, notably an aromatic ring, with the carbon atoms of the imidazole ring to which they are attached.

14. Modified polymer according to any one of the preceding embodiments, in which Y and Z are a hydrogen atom.

15. Modified polymer according to any one of embodiments 1 to 13, in which the groups Y and Z together form an aromatic ring with the carbon atoms of the imidazole ring to which they are attached; preferably, the groups Y and Z form a benzene ring with the carbon atoms of the imidazole ring to which they are attached.

16. Modified polymer according to any one of the preceding embodiments, in which $R_1$ is a hydrogen atom or a $C_1$-$C_6$ alkyl, preferably methyl.

17. Modified polymer according to any one of the preceding embodiments, characterized in that it is the compound of formula (VIII)

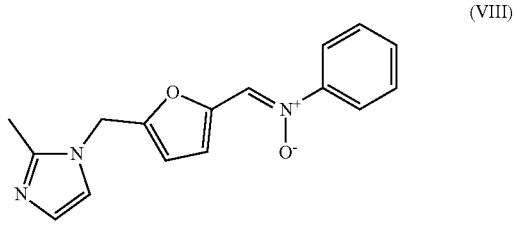 [SMILES: Cc1nccn1Cc1ccc(/C=[N+](\[O-])c2ccccc2)o1]

(VIII)

18. Modified polymer according to any one of the preceding embodiments, in which the initial polymer is an elastomer, preferably a diene elastomer.

19. Modified polymer according to embodiment 18, in which the diene elastomer is chosen from the group consisting of ethylene/propylene/diene monomer copolymers, butyl rubber, natural rubber, synthetic polyisoprenes, polybutadienes, butadiene copolymers, isoprene copolymers and mixtures of these elastomers.

20. Process for preparing a modified polymer according to any one of the preceding embodiments, said process comprising a step of grafting, onto an initial polymer comprising at least one unsaturation, of a compound of formula (I), by [3+2] cycloaddition of the function Q of the compound of formula (I) on said unsaturation

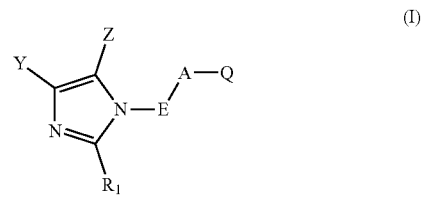

(I)

in which:

Q represents a dipole comprising at least one nitrogen atom;

A represents a divalent heteroaromatic ring optionally substituted with one or more identical or different linear or branched aliphatic hydrocarbon-based chains, optionally substituted or interrupted with one or more heteroatoms;

E represents a divalent hydrocarbon-based group which may optionally contain one or more heteroatoms;

$R_1$ represents a hydrogen atom or a $C_1$-$C_{20}$ alkyl group; and

Y and Z, which may be identical or different, each represent a hydrogen atom or a hydrocarbon-based chain, Y and Z together also possibly forming a ring, notably an aromatic ring, with the carbon atoms of the imidazole ring to which they are attached.

21. Process for preparing a modified polymer according to embodiment 20, in which the compound of formula (I) is chosen from the compounds of formula (IIa)

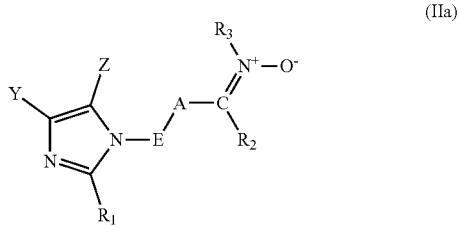

(IIa)

in which:
A represents a divalent heteroaromatic ring optionally substituted with one or more identical or different linear or branched aliphatic hydrocarbon-based chains, optionally substituted or interrupted with one or more heteroatoms;
E represents a divalent hydrocarbon-based group which may optionally contain one or more heteroatoms;
$R_1$ represents a hydrogen atom or a $C_1$-$C_{20}$ alkyl group;
Y and Z, which may be identical or different, each represent a hydrogen atom or a hydrocarbon-based chain, Y and Z together also possibly forming a ring, notably an aromatic ring, with the carbon atoms of the imidazole ring to which they are attached;
$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and
$R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

22. Process for preparing a modified polymer according to either of embodiments 20 and 21, in which A is a divalent heteroaromatic ring formed from 5 to 10 atoms, preferably from 5 to 6 atoms, optionally substituted with one or more identical or different linear or branched, aliphatic $C_1$-$C_{24}$ hydrocarbon-based chains, optionally substituted or interrupted with one or more heteroatoms.

23. Process for preparing a modified polymer according to one of embodiments 20 to 22, in which the compound of formula (IIa) is chosen from those of formula (IIb)

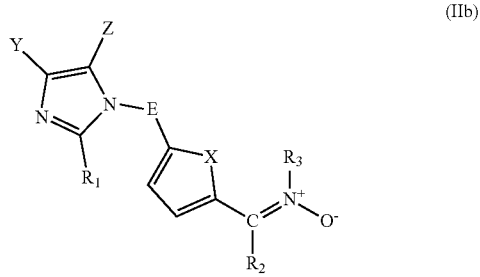

(IIb)

in which:
X represents a heteroatom group chosen from a sulfur atom, an oxygen atom and a nitrogen atom; preferably, X is an oxygen atom;
E represents a divalent hydrocarbon-based group which may optionally contain one or more heteroatoms;
$R_1$ represents a hydrogen atom or a $C_1$-$C_{20}$ alkyl group;
Y and Z, which may be identical or different, each represent a hydrogen atom or a hydrocarbon-based chain, Y and Z together also possibly forming a ring, notably an aromatic ring, with the carbon atoms of the imidazole ring to which they are attached;
$R_2$ is chosen from a hydrogen atom, a linear or branched $C_1$-$C_{20}$ alkyl, a $C_3$-$C_{20}$ cycloalkyl optionally substituted with one or more aliphatic hydrocarbon-based chains, which are preferably saturated, linear or branched, and a $C_6$-$C_{20}$ aryl optionally substituted with one or more aliphatic hydrocarbon-based chains, which are preferably saturated, linear or branched; and
$R_3$ is chosen from the group consisting of linear or branched $C_1$-$C_{20}$ alkyls, $C_3$-$C_{20}$ cycloalkyls optionally substituted with one or more aliphatic hydrocarbon-based chains, which are preferably saturated, linear or branched, and $C_6$-$C_{20}$ aryls optionally substituted with one or more aliphatic hydrocarbon-based chains, which are preferably saturated, linear or branched.

24. Process for preparing a modified polymer according to any one of embodiments 20 to 23, characterized in that the compound of formula (I) is the compound of formula (VIII)

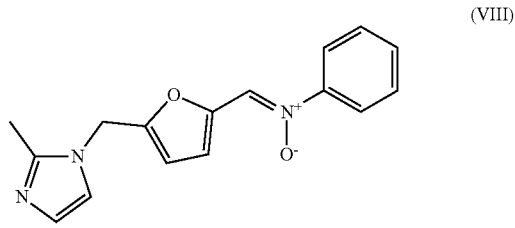 [SMILES: Cc1nccn1Cc1ccc(/C=[N+](\[O-])c2ccccc2)o1]

(VIII)

25. Composition comprising at least one modified polymer according to any one of the preceding embodiments 1 to 19 and at least one additive, the additive is preferably a filler, even more preferentially the additive is a reinforcing filler, even more preferentially the additive is an inorganic reinforcing filler, more preferentially the additive is a silica.

26. Tread comprising at least one composition as defined in embodiment 25.

27. Tyre comprising at least one composition as defined in embodiment 25.

28. Tyre comprising at least one tread as defined in embodiment 26.

V—EXAMPLES

The examples which follow make it possible to illustrate the invention; however, the invention shall not be limited to these examples alone.

5.1 Characterizations of the Molecules

The structural analysis and the determination of the molar purities of the molecules synthesized are performed by NMR analysis. The spectra are acquired on a Brüker Avance 3 400 MHz spectrometer equipped with a "5 mm BBFO Z-grad broad band" probe. The quantitative $^1$H NMR experiment uses a simple 30° pulse sequence and a repetition delay of 3 seconds between each of the 64 acquisitions. The samples are dissolved in a deuterated solvent, deuterated dimethyl sulfoxide (DMSO), unless otherwise indicated.

The deuterated solvent is also used for the "lock" signal. For example, calibration is performed on the signal of the protons of the deuterated DMSO at 2.44 ppm relative to a TMS reference at 0 ppm. The $^1$H NMR spectrum coupled with the 2D $^1$H/$^{13}$C HSQC and $^1$H/$^{13}$C HMBC experiments enable the structural determination of the molecules (cf. assignment tables). The molar quantifications are performed from the quantitative 1D $^1$H NMR spectrum.

5.2 Characterization of the Molecules Grafted onto a Diene Elastomer

The determination of the molar content of the grafted compound tested on a diene elastomer is performed by NMR analysis. The spectra are acquired on a Brüker 500 MHz spectrometer equipped with a "5 mm BBFO Z-grad Cryo-Probe" probe. The quantitative $^1$H NMR experiment uses a simple 30° pulse sequence and a repetition delay of 5 seconds between each acquisition. The samples are dissolved in a deuterated solvent, deuterated chloroform (CDCl$_3$) unless indicated otherwise, for the purpose of obtaining a "lock" signal. 2D NMR experiments made it possible to confirm the nature of the grafted unit by means of the chemical shifts of the carbon atoms and protons.

5.3 Measurement of the Number-Average (Mn) and Weight-Average (Mw) Molar Masses and of the Polydispersity Index of the Diene Elastomers Unless expressly indicated otherwise, the number-average and weight-average molar masses of the diene elastomers used are measured by the size exclusion chromatography (SEC) technique. SEC makes it possible to separate macromolecules in solution according to their size through columns filled with a porous gel. The macromolecules are separated according to their hydrodynamic volume, the bulkiest being eluted first.

Without being an absolute method, SEC makes it possible to comprehend the molar mass distribution of an elastomer. The various number-average molar masses (Mn) and weight-average molar masses (Mw) may be determined from commercial standards and the polydispersity index (PI=Mw/Mn) may be calculated via a "Moore" calibration.

There is no specific treatment for the elastomer sample before analysis. Said sample is simply dissolved to a concentration of about 1 g/l, in chloroform or in the following mixture: tetrahydrofuran+1 vol % of diisopropylamine+1 vol % of triethylamine+1 vol % of distilled water (vol %=% by volume). The solution is then filtered through a filter with a porosity of 0.45 μm before injection.

The apparatus used is a Waters Alliance chromatograph. The elution solvent is the following mixture: tetrahydrofuran+1 vol % of diisopropylamine+1 vol % of triethylamine or chloroform according to the solvent used for dissolving the elastomer. The flow rate is 0.7 ml/min, the temperature of the system is 35° C. and the analysis time is 90 min. A set of four Waters columns in series, having the commercial names Styragel HMW7, Styragel HMW6E and two Styragel HT6E, is used.

The volume of the solution of the elastomer sample injected is 100 The detector is a Waters 2410 differential refractometer at a wavelength of 810 nm. The software for processing the chromatographic data is the Waters Empower system.

The calculated average molar masses are relative to a calibration curve produced from PSS Ready Cal-Kit commercial polystyrene standards.

5.4 Synthesis of 1-(5-((2-methyl-1H-imidazol-1-yl) methylfuran-2-yl)-N-phenylmethanimine oxide (Compound E)

1-(5-((2-Methyl-1H-imidazol-1-yl)methylfuran-2-yl)-N-phenylmethanimine oxide may be synthesized according to the following reaction scheme

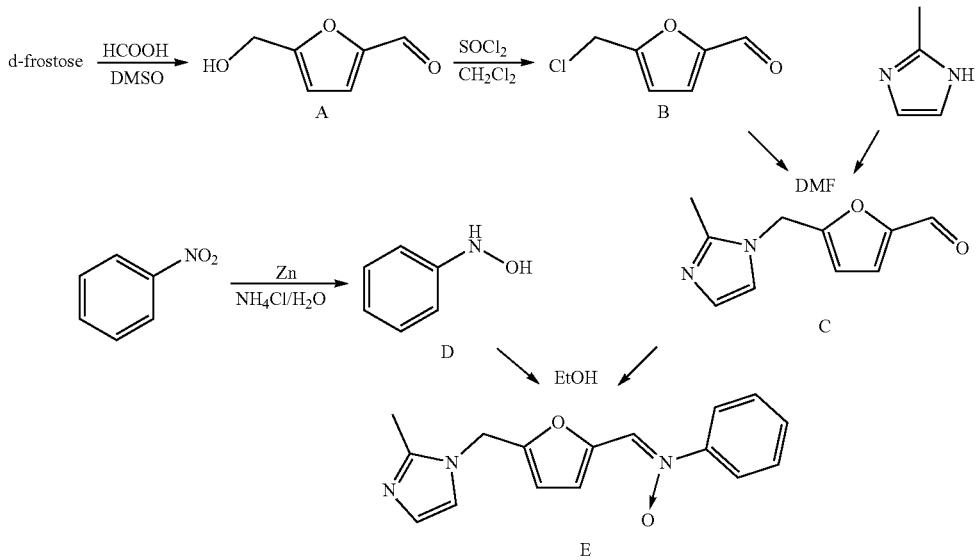

1-(5-((2-Methyl-1H-imidazol-1-yl)methylfuran-2-yl)-N-phenylmethanimine oxide is synthesized in two steps which are described below. All the chemical compounds used during this synthesis are obtained from "Sigma-Aldrich" or from "Fischer Scientific".

5-(Hydroxymethyl) furan-2-carbaldehyde (compound A, CAS 67-47-0) is commercial or may be synthesized biochemically or chemically from fructose.

The product N-phenylhydroxylamine (compound D, CAS 100-65-2) is commercial or may be synthesized from nitrobenzene according to the procedure described in Organic Syntheses, Coll. Vol. 1, page 445 (1941); Vol. 4, page 57 (1925).

5-(Chloromethyl) furan-2-carbaldehyde (compound B) may be synthesized from fructose or from 5-(hydroxymethyl) furan-2-carbaldehyde according to the procedure described in Sanda, Komla et al., Synthesis of 5-(bromomethyl)- and of 5-(chloromethyl)-2-furancarboxaldehyde, Carbohydrate Research, 187 (1), 15-23; 1989

5.4.1 Step 1: Synthesis of 5-((2-methyl-1H-imidazol-1-yl)methyl)furan-2-carbaldehyde (Product C)

A mixture of 2-methylimidazole (4.83 g; 58.80 mmol; 2.5 eq.) and 5-(chloromethyl) furan-2-carbaldehyde (3.40 g; 23.52 mmol) in DMF (4 ml) is heated to a bath temperature of 70° C. After stirring for 2-3 hours at this temperature and 2 hours at a bath temperature of 80° C., the reaction medium is diluted with water (50 ml) and the organic phase is then separated out. The aqueous phase is extracted four times with dichloromethane (four times 20 ml). The organic phase fractions are combined and then washed with water (four times 5 ml) and then concentrated under reduced pressure (2-3 mbar; 32° C.) to give a black-coloured oil (2.44 g; 12.8 mmol) in a yield of 55%. This product is engaged in the following step without further purification.

5.4.2 Step 2: Synthesis of 1-(5-((2-methyl-1H-imidazol-1-yl)methyl)furan-2-yl)-N-phenylmethanimine oxide (Product E)

To a solution of 5-((2-methyl-1H-imidazol-1-yl)methyl) furan-2-carbaldehyde (compound C) (5.00 g; 26.3 mmol) in ethanol (5 ml) at a bath temperature of 35-40° C. is added N-phenylhydroxylamine (2.87 g; 26.3 mmol; 1 eq.) portionwise over 5 minutes. The reaction medium is heated up to a bath temperature of 60° C. After stirring for 1.5 hours at this temperature and then returning to a temperature of 30-35° C., tert-butyl methyl ether (15 ml) is added dropwise. After stirring for one hour at room temperature (23° C.), the precipitate obtained is filtered off and washed on the filter with a mixture of ethanol and tert-butyl methyl ether (1 ml and 5 ml) and then with tert-butyl methyl ether (8 ml). A light-brown solid with a melting point of 147-150° C. is obtained in a yield of 68.4% (5.06 g; 17.99 mmol) and a molar purity of greater than 98% ($^1$H NMR).

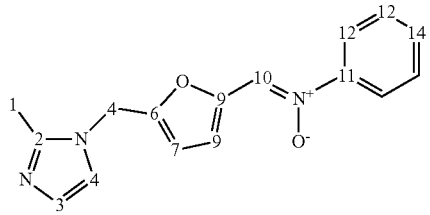

TABLE 1

| No. | δ $^1$H (ppm) | δ $^{13}$C (ppm) |
|---|---|---|
| 1 | 2.37 | 12.6 |
| 2 | / | 144.2 |
| 3 | 6.87 | 127.1 |
| 4 | 6.81 | 119.0 |
| 5 | 4.99 | 42.6 |
| 6 | / | 150.7 |
| 7 | 6.39 | 110.8 |
| 8 | 7.87 | 116.4 |
| 9 | / | 147.5 |
| 10 | 8.01 | 123.1 |
| 11 | / | 146.7 |
| 12 | 7.71 | 120.5 |
| 13 | 7.41 | 128.7 |
| 14 | 7.40 | 129.6 |

5.5 Grafting of Polymer with Compound E

5.5.1 Manufacture of a styrene-butadiene Copolymer Grafted with 1-(5-((2-methyl-1H-imidazol-1-yl)methyl)furan-2-yl)-N-phenylmethanimine oxide (Compound E)

1-(5-((2-Methyl-1H-imidazol-1-yl)methyl)furan-2-yl)-N-phenylmethanimine oxide (0.31; 1.14 mmol) is incorporated into 15 g of a styrene-butadiene copolymer SBR (containing 26.5% by weight of styrene relative to the total weight of the copolymer and 24% by weight of 1,2-butadiene units relative to the weight of the butadiene part, 28% by weight of 1,4-cis-butadiene units relative to the weight of the butadiene part and 48% by weight of 1,4-trans-butadiene units relative to the weight of the butadiene part, Mn=120 000 g/mol and PI=1.84 measured according to the method described in paragraph 5.3) on a roll mill at 23° C. The mixture is homogenized by 15 portfolio passes. This mixing phase is followed by a heat treatment at 160° C. for 60 minutes under a press at a pressure of 10 bar.

The grafting results according to the $^1$H NMR analysis are presented in Table 2.

5.5.2 Manufacture of a Polybutadiene Polymer Grafted with 1-(5-((2-methyl-1H-imidazol-1-yl)methyl)furan-2-yl)-N-phenylmethanimine oxide (Compound E)

0.5 g of polybutadiene (75.4 mol % of 1,2-butadiene units and 24.6 mol % of 1,4-butadiene units; Mn=7800 g/mol and PI=1.02 measured according to the method described in paragraph 5.3) were flushed with nitrogen for 15 minutes. Next, 2 ml of dichloromethane, sparged beforehand with nitrogen for 5 minutes, were added to dissolve this polymer.

Once this polymer was dissolved, 0.265 g of 1-(5-((2-methyl-1H-imidazol-1-yl)methyl)furan-2-yl)-N-phenylmethanimine oxide (compound E) (0.94 mmol) dissolved beforehand in 2 ml of dichloromethane was added to the reaction medium with stirring. After stirring for 15 minutes, the reaction medium was left under a flush of nitrogen for 15 minutes to evaporate off the dichloromethane. Once all of the solvent was evaporated off, the reaction medium was heated to 150° C. (bath temperature) under a constant stream of nitrogen. After reaction for 10 hours 30 minutes, the reaction medium was allowed to return to room temperature (23° C.).

The grafting results according to the $^1$H NMR analysis are presented in Table 2.

5.5.3 Manufacture of an ethylene-butadiene Copolymer Grafted with 1-(5-((2-methyl-1H-imidazol-1-yl)methyl)furan-2-yl)-N-phenylmethanimine oxide (Compound E)

1-(5-((2-Methyl-1H-imidazol-1-yl)methyl)furan-2-yl)-N-phenylmethanimine oxide (0.57; 2 mmol) is incorporated into 15 g of an ethylene-butadiene copolymer EBR (containing 16.8 mol % of butadiene, 7.7 mol % of butadiene/ethylene rings and 75.5 mol % of ethylene) on a roll mill at 23° C. The mixture is homogenized by 15 portfolio passes. This mixing phase is followed by a heat treatment at 160° C. for 60 minutes under a press at a pressure of 10 bar.

The grafting results according to the $^1$H NMR analysis are presented in Table 2.

TABLE 2

| Elastomer | Targeted degree (mol %) | Grafted compound E (mol %) | Grafting yield (%) |
|---|---|---|---|
| BR | 10 | 9.3 | 93% |
| EBR | 0.5 | 0.31 | 62% |
| SBR | 0.47 | 0.37 | 78% |

5.6. Synthesis of the 1,3-Dipolar Compound N-(4-((2-methyl-1H-imidazol-1-yl)methyl)benzylidene) aniline oxide (Compound E1)

This compound may be prepared in five steps according to the following reaction scheme:

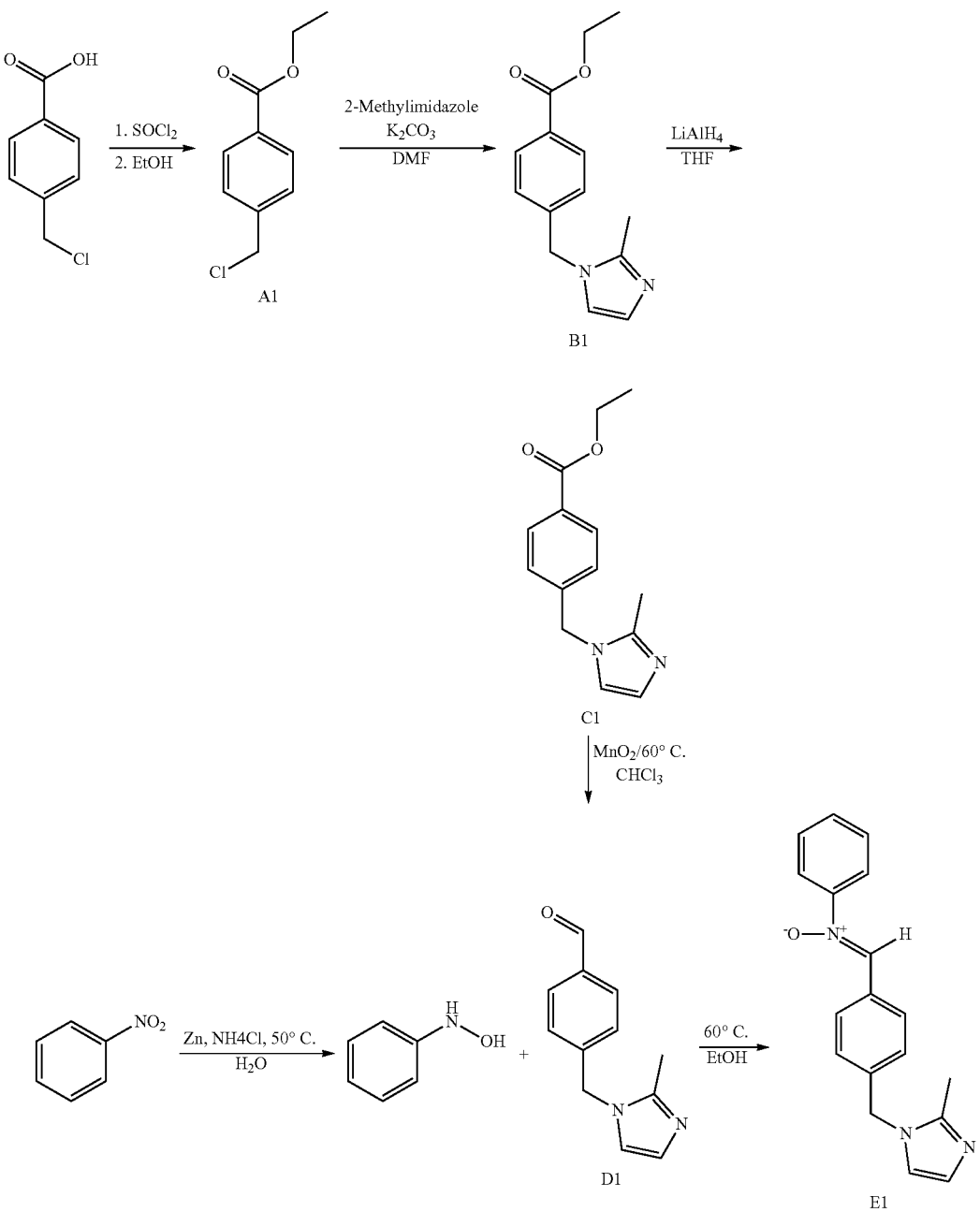

5.6.1 Step 1: Synthesis of methyl 4-(chloromethyl)benzoate (Compound A1)

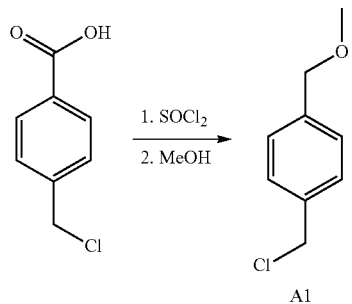

A1

Thionyl chloride SOCl$_2$ (2.4 ml; 32.2 mmol) is added dropwise over 10 minutes at a temperature of −8° C. (bath temperature) to 150 ml of methanol cooled to a temperature of −8° C. (bath temperature). After stirring for 5 minutes at −8° C. (bath temperature), 4-(chloromethyl)benzoic acid (5.0 g; 29.3 mmol) is added portionwise over 10 minutes at −8° C. (bath temperature). After stirring for 20 minutes at −8° C. (bath temperature), the reaction medium is heated at 14° C. (bath temperature) for 20 minutes. The reaction medium is then heated up to 50° C. (bath temperature) over 1 hour and is stirred at this temperature for 2 hours. The product solution is concentrated under reduced pressure (28 mbar, 40° C., bath temperature) to give an oil which crystallizes at room temperature.

A white solid (5.16 g, 27.9 mmol, molar yield of 95%) with a melting point of 38-40° C. is obtained.

The molar purity is greater than 95 mol % ($^1$H NMR).

TABLE 3

| No. | δ $^1$H (ppm) | δ $^{13}$C (ppm) |
|---|---|---|
| 1 | 3.92 | 45.4 |
| 2 | / | 166.5 |
| 3 | / | 128.5 |
| 4 | 8.04 | 130.0 |
| 5 | 7.47 | 129.2 |
| 6 | / | 142.2 |
| 7 | 4.62 | 52.2 |

Solvent: CDCl$_3$

5.6.2 Step 2: Synthesis of methyl-4-((2-methyl-1H-imidazol-1-yl)methyl)benzoate

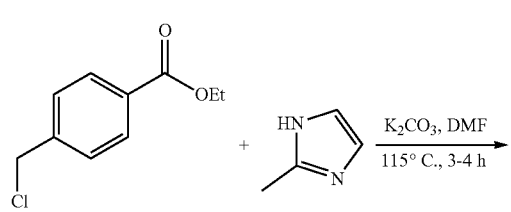

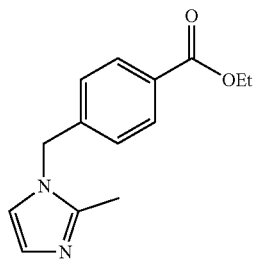

A mixture of methyl 4-(chloromethyl)benzoate (5.15 g; 28 mmol) and 2-methyl-1H-imidazole (2.52 g; 31 mmol) and K$_2$CO$_3$ (2.89 g; 21 mmol) in DMF (4 ml) is heated at 60° C. (bath temperature) for 1-1.5 hours, and then for 5 hours at 80° C. After cooling, the reaction medium is diluted with water at 0° C. (50 ml) and ethyl acetate (25 ml). The aqueous phase is separated out and extracted with ethyl acetate (3 times 10 ml). The combined organic phases are washed with water (3 times 5 ml). The product solution is concentrated under reduced pressure (7 mbar, 40° C., bath temperature) to give a yellow oil (4.266 g; 18.5 mmol, molar yield of 66%).

TABLE 4

| No. | δ $^1$H (ppm) |
|---|---|
| 1 | 5.09 |
| 2 | / |
| 3 | 7.08 |
| 4 | 7.99 |
| 5 | / |
| 6 | / |
| 7 | 3.46 |
| 8 | 7.99 |
| 9 | 7.08 |
| 10 | 6.96 |
| 11 | 6.84 |
| 12 | / |
| 13 | 2.30 |

Solvent: CDCl$_3$

5.6.3 Step 3: Synthesis of 4-((2-methyl-1H-imidazol-1-yl)methyl)phenylmethanol

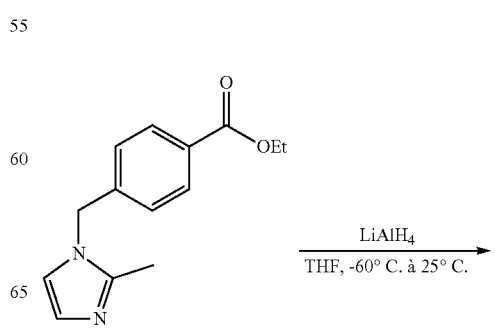

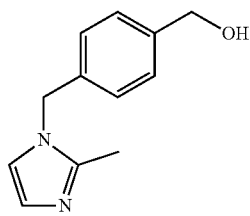

A solution of LiAlH₄ (1.50 g, 0.039 mol) in anhydrous THF (230 ml) is cooled to −60° C. A solution of ethyl 4-((2-methyl-1H-imidazol-1-yl)methyl)benzoate (7.80 g, 0.028 mol, 81 mol %) in anhydrous THF (100 ml) is added under argon over 15 minutes. The reaction medium is stirred 1 hour at −60° C. for and then for 10-12 hours at room temperature. Water (20 ml) is added dropwise (an exothermic reaction). The precipitate formed is filtered off and the filtrate is concentrated under reduced pressure. The crude product obtained is dissolved in CH₂Cl₂ (100 ml) in order to precipitate the insoluble materials. After filtering and concentrating under reduced pressure, a yellow oil (4.96 g, molar yield of 93%) is obtained. The molar purity is greater than 85% NMR).

TABLE 5

| No. | δ ¹H (ppm) |
|---|---|
| 1 | 4.99 |
| 2 | / |
| 3 | 7.30 |
| 4 | 6.97 |
| 5 | / |
| 6 | 4.66 |
| 7 | 7.63 |
| 8 | 6.97 |
| 9 | 7.30 |
| 10 | 6.82 |
| 11 | 6.79 |
| 12 | / |
| 13 | 2.23 |

Solvent: CDCl₃

5.6.4 Step 4: Synthesis of 4-((2-methyl-1H-imidazol-1-yl)methyl)benzaldehyde

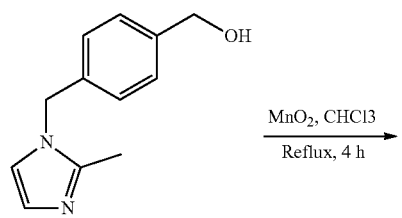

A mixture of MnO₂ (6.88 g; 0.079 mol) and 4-((2-methyl-1H-imidazol-1-yl)methyl)phenylmethanol (4.57 g; 0.021 mol, 85 mol % by ¹H NMR) in CHCl₃ (180 ml) is stirred at reflux temperature for 4 hours. The reaction medium is cooled to room temperature and is kept stirring at this temperature for 10-12 hours. The insoluble products are filtered off and the filtrate is concentrated under reduced pressure. A yellow oil (3.78 g, molar yield of 98%) is obtained after concentrating under reduced pressure. The molar purity is greater than 81% (¹H NMR).

TABLE 6

| No. | δ ¹H (ppm) |
|---|---|
| 1 | 5.16 |
| 2 | / |
| 3 | 7.20 |
| 4 | 7.89 |
| 5 | / |
| 6 | 10.01 |
| 7 | 7.89 |
| 8 | 7.20 |
| 9 | 7.02 |
| 10 | 6.88 |
| 11 | / |
| 12 | 2.34 |

Solvent: CDCl₃

5.6.5 Synthesis of Phenylhydroxylamine

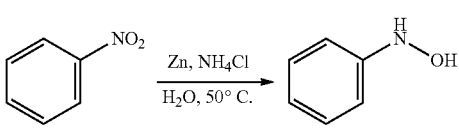 [SMILES: O=[N+]([O-])c1ccccc1 ; ONc1ccccc1]

Phenylhydroxylamine was synthesized according to the procedure described in Org. Syntheses Coll. Vol. 1, page 445, 1941; Org. Syntheses Coll. Vol. 3, page 668, 1955.

5.6.6 Step 5: Synthesis of N-4-((2-methyl-1H-imidazol-1-yl))methyl)benzyldiene)aniline oxide

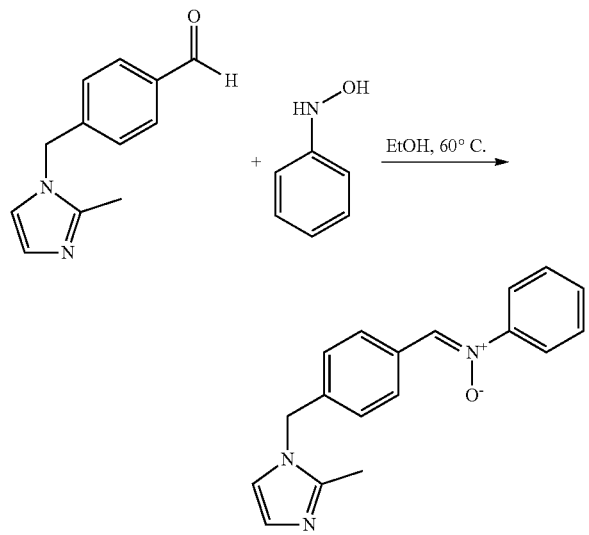

A solution of 4-((2-methyl-1H-imidazol-1-yl))methyl)benzaldehyde (3.48 g; 0.015 mol, 81 mol % by $^1$H NMR) and phenylhydroxylamine (2.86 g; 0.026 mol) in anhydrous ethanol (20 ml) is stirred for 2 hours at 60° C. (bath temperature) and then for 12 hours at room temperature. The yellow precipitate is filtered off (0.249 g, containing the expected product). Water (30 ml) is added to the filtrate with vigorous stirring. The yellow precipitate then formed is filtered off after stirring for 20 minutes and is washed with a mixture of EtOH (10 ml) and water (20 ml) and then with water (50 ml). The two portions of solid are combined and dried under atmospheric pressure at room temperature for 10-12 hours. A yellow solid (3.71 g, molar yield 89%) with a molar purity of greater than 82% ($^1$H NMR) is obtained. An additional purification is applied by stirring at room temperature for 1.5 hours, filtering, washing on the filter with 50 ml of ethyl ether and drying for 2 days at room temperature.

A yellow solid (3.04 g, molar yield 78%) with a melting point of 115-116° C. is obtained. The molar purity is greater than 88% ($^1$H NMR).

TABLE 7

| No. | δ $^1$H (ppm) | δ $^{13}$C (ppm) |
|---|---|---|
| 1 | 2.28 | 13.1 |
| 2 | / | 145.0 |
| 3 | 6.93 | 127.6 |
| 4 | 6.81 | 119.9 |
| 5 | 5.05 | 49.6 |
| 6 | / | 139.0 |
| 7 | 7.11 | 126.8 |
| 8 | 8.32 | 129.5 |
| 9 | / | 130.5 |
| 10 | 7.85 | 133.6 |
| 11 | / | 149.1 |
| 12 | 7.72 | 121.7 |
| 13 | 7.43 | 129.2 |
| 14 | 7.42 | 130.1 |

Solvent: CDCl$_3$

5.7. Study of the Grafting Yield of Compound E as a Function of Time

In this test, the grafting yield as a function of time of a 1,3-dipolar compound according to the invention (compound E) is compared, on a styrene/butadiene copolymer SBR, with that of a 1,3-dipolar compound of the prior art (Compound E1).

A styrene/butadiene copolymer used is an SBR containing 26.5% by weight of styrene relative to the total weight of the copolymer and in its butadiene part, relative to the weight of the butadiene part, 24% by weight of 1,2-butadiene units, 28% by weight of 1,4-cis-butadiene units and 48% by weight of 1,4-trans-butadiene units relative to the weight of the butadiene part. Its Mn is equal to 120 000 g/mol and its PI is equal to 1.84; they are measured according to the method described in paragraph 3.

The process is performed in the following manner:

1-(5-((2-Methyl-1H-imidazol-1-yl)methyl)furan-2-yl)-N-phenylmethanimine oxide (0.27 g, 0.97 mmol) (compound E according to the invention) or N-(4-((2-methyl-1H-imidazol-1-yl)methyl)benzylidene)aniline oxide (compound E1 not in accordance) (0.28 g, 0.97 mmol) is incorporated into 15 g of SBR as described above on a roll mill at 23° C. The mixture is homogenized by 15 portfolio passes. This mixing phase is followed by a heat treatment at 160° C. for 15 minutes under a press at a pressure of 10 bar.

The same experiment is performed for grafting times of 30 minutes and 60 minutes.

At the end of each experiment, the molar degree of grafting of compound E, in accordance with the invention, or of compound E1, not in accordance with the invention, is determined analytically by $^1$H NMR in accordance with the method described in paragraph 2. The results are collated in Table 8.

TABLE 8

| Grafting time | Grafting yield (%) | | |
| --- | --- | --- | --- |
| | 15 min | 30 min | 60 min |
| Compound E | 60 | 67 | 78 |
| Compound E1 | 44 | 46 | 44 |

Surprisingly, it is seen from Table 8 that the grafting yield of compound E in accordance with the invention is always significantly improved relative to compound E1 not in accordance with the invention. In addition, the grafting yield of compound E in accordance with the invention continues to increase beyond the 30 minutes of reaction, whereas a plateau is reached within 15 minutes for compound E1 not in accordance with the invention.

The invention claimed is:

1. A modified polymer obtained by grafting of at least one compound of formula (I) onto at least one unsaturation of an initial polymer chain

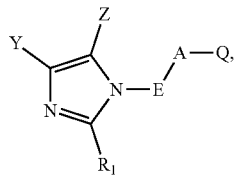
(I)

in which:
- Q represents a dipole comprising at least one nitrogen atom;
- A represents a divalent heteroaromatic ring optionally substituted with one or more identical or different linear or branched aliphatic hydrocarbon-based chains, optionally substituted or interrupted with one or more heteroatoms;
- E represents a divalent hydrocarbon-based group which may optionally contain one or more heteroatoms;
- $R_1$ represents a hydrogen atom or a $C_1$-$C_{20}$ alkyl group; and
- Y and Z, which may be identical or different, each represent a hydrogen atom or a hydrocarbon-based chain, or Y and Z together form a ring with the carbon atoms of the imidazole ring to which they are attached.

2. The modified polymer according to claim 1, wherein a molar degree of grafting of the compound of formula (I) is in a range extending from 0.01% to 15%.

3. The modified polymer according to claim 1, wherein Q is a group of formula (II), (III) or (IV)

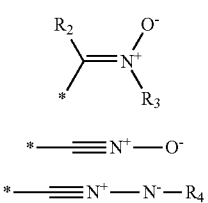
(II)

(III)

(IV)

in which:
- the symbol * represents the attachment of Q to A;
- $R_2$ and $R_4$ are selected, independently of each other, from a hydrogen atom, a linear or branched $C_1$-$C_{20}$ alkyl, a $C_3$-$C_{20}$ cycloalkyl optionally substituted with one or more aliphatic hydrocarbon-based chains, which are optionally saturated, linear or branched, and a $C_6$-$C_{20}$ aryl optionally substituted with one or more aliphatic hydrocarbon-based chains; and
- $R_3$ is selected from the group consisting of linear or branched $C_1$-$C_{20}$ alkyls, $C_3$-$C_{20}$ cycloalkyls optionally substituted with one or more aliphatic hydrocarbon-based chains, and $C_6$-$C_{20}$ aryls optionally substituted with one or more aliphatic hydrocarbon-based chains.

4. The modified polymer according to claim 3, wherein the compound of formula (I) is chosen from the compounds of formula (IIa)

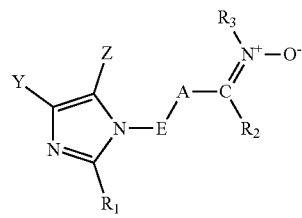
(IIa)

in which:
- A represents a divalent heteroaromatic ring optionally substituted with one or more identical or different linear or branched aliphatic hydrocarbon-based chains, optionally substituted or interrupted with one or more heteroatoms;
- E represents a divalent hydrocarbon-based group which may optionally contain one or more heteroatoms;
- $R_1$ represents a hydrogen atom or a $C_1$-$C_{20}$ alkyl group;
- Y and Z, which may be identical or different, each represent a hydrogen atom or a hydrocarbon-based chain, or Y and Z together form a ring with the carbon atoms of the imidazole ring to which they are attached;
- $R_2$ is selected from a hydrogen atom, a linear or branched $C_1$-$C_{20}$ alkyl, a $C_3$-$C_{20}$ cycloalkyl optionally substituted with one or more aliphatic hydrocarbon-based chains, and a $C_6$-$C_{20}$ aryl optionally substituted with one or more aliphatic hydrocarbon-based chains; and
- $R_3$ is selected from the group consisting of linear or branched $C_1$-$C_{20}$ alkyls, $C_3$-$C_{20}$ cycloalkyls optionally substituted with one or more aliphatic hydrocarbon-based chains, and $C_6$-$C_{20}$ aryls optionally substituted with one or more aliphatic hydrocarbon-based chains.

5. The modified polymer according to claim 1, wherein A is a divalent heteroaromatic ring formed from 5 to 10 atoms, optionally substituted with one or more identical or different linear or branched, aliphatic $C_1$-$C_{24}$ hydrocarbon-based chains, optionally substituted or interrupted with one or more heteroatoms.

6. The modified polymer according to claim 4, wherein the compound of formula (IIa) is selected from compounds of formula (IIb)

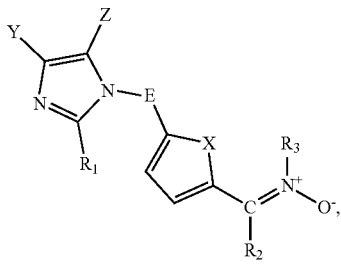

(IIb)

in which:
- X represents a heteroatom selected from a sulfur atom, an oxygen atom and a nitrogen atom;
- E represents a divalent hydrocarbon-based group which may optionally contain one or more heteroatoms;
- $R_1$ represents a hydrogen atom or a $C_1$-$C_{20}$ alkyl group;
- Y and Z, which may be identical or different, each represent a hydrogen atom or a hydrocarbon-based chain, or Y and Z together form a ring with the carbon atoms of the imidazole ring to which they are attached;
- $R_2$ is selected from a hydrogen atom, a linear or branched $C_1$-$C_{20}$ alkyl, a $C_3$-$C_{20}$ cycloalkyl optionally substituted with one or more aliphatic hydrocarbon-based chains, and a $C_6$-$C_{20}$ aryl optionally substituted with one or more aliphatic hydrocarbon-based chains; and
- $R_3$ is selected from the group consisting of linear or branched $C_1$-$C_{20}$ alkyls, $C_3$-$C_{20}$ cycloalkyls optionally substituted with one or more aliphatic hydrocarbon-based chains, and $C_6$-$C_{20}$ aryls optionally substituted with one or more aliphatic hydrocarbon-based chains.

7. The modified polymer according to claim 3, wherein $R_2$ is a hydrogen atom and $R_3$ is selected from $C_1$-$C_{20}$ alkyls and $C_6$-$C_{20}$ aryls.

8. The modified polymer according to claim 1, wherein E is selected from linear or branched, saturated aliphatic $C_1$-$C_{24}$, optionally interrupted with one or more nitrogen, sulfur or oxygen atoms.

9. The modified polymer according to claim 1, wherein E is selected from the groups —R—, —NHR—, —OR— and —SR—, where R is a linear or branched $C_1$-$C_{24}$ alkylene.

10. The modified polymer according to claim 1, wherein Y and Z, which may be identical or different, each represent a hydrogen atom or a linear or branched $C_1$-$C_{24}$ alkyl, or Y and Z together form a ring with the carbon atoms of the imidazole ring to which they are attached.

11. The modified polymer according to claim 1, wherein Y and Z are a hydrogen atom.

12. The modified polymer according to claim 1, wherein $R_1$ is a hydrogen atom or a $C_1$-$C_6$ alkyl.

13. The modified polymer according to claim 1, wherein the compound of formula (I) is the compound of formula (VIII)

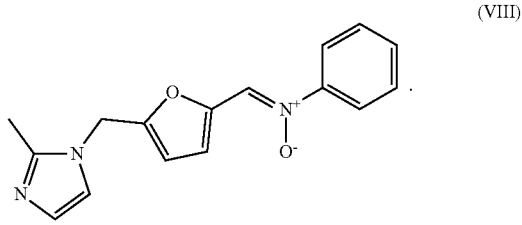 [SMILES: Cc1nccn1Cc1ccc(/C=[N+](\[O-])c2ccccc2)o1]

(VIII)

14. The modified polymer according to claim 1, wherein the initial polymer is an elastomer.

15. A composition comprising at least one modified polymer according to claim 1 and at least one additive.

* * * * *